United States Patent

Arosio et al.

[11] Patent Number: 5,847,214
[45] Date of Patent: Dec. 8, 1998

[54] PROCESS FOR PREPARING N-METHYL-3-(P-TRIFLUOROMETHYLPHENOXY)-3-PHENYL-PROPYLAMINE AND SALTS THEREOF IN A HIGHLY PURE FORM

[75] Inventors: Roberto Arosio, Civate; Stefano Giovanni Vittorio Beratto; Vittorio Rossetti, both of Milan, all of Italy

[73] Assignee: Laporte Organics Francis S.p.A., Milan, Italy

[21] Appl. No.: 889,162

[22] Filed: Jul. 7, 1997

[30] Foreign Application Priority Data

Jul. 11, 1996 [IT] Italy .................................. MI96A1438

[51] Int. Cl.$^6$ ........................ C07C 213/06; C07C 217/48
[52] U.S. Cl. ............................................................. 564/347
[58] Field of Search ................................................ 564/347

[56] References Cited

U.S. PATENT DOCUMENTS

| 4,314,081 | 2/1982 | Molloy et al. | 564/347 |
| 5,166,437 | 11/1992 | Kairisalo et al. | 564/347 |
| 5,618,968 | 4/1997 | Crnic et al. | 560/27 |

FOREIGN PATENT DOCUMENTS

WO 94/00416  1/1994  WIPO .

*Primary Examiner*—Richard L. Raymond
*Attorney, Agent, or Firm*—Guido Modiano; Albert Josif

[57] ABSTRACT

The present invention relates to a process for preparing N-methyl-3-(p-trifluoromethylphenoxy)-3-phenyl-propylamine and pharmaceutically acceptable acid addition salts thereof. The process in accordance with the present invention comprises reacting 1-phenyl-3-(N-methylamine) propane-1-ol with 1-chloro-4-trifluoromethylbenzene, in the presence of an hydroxide of an alkaline metal in a dipolar aprotic solvent non saponifiable in reaction conditions. The process in accordance with the present invention further comprises a final crystallization step which allows to obtain the active ingredient in a highly pure crystalline form.

13 Claims, No Drawings

PROCESS FOR PREPARING N-METHYL-3-(P-TRIFLUOROMETHYLPHENOXY)-3-PHENYL-PROPYLAMINE AND SALTS THEREOF IN A HIGHLY PURE FORM

The present invention relates to a process for preparing N-methyl-3-(p-trifluoromethylphenoxy)-3-phenyl-propylamine of formula (I)

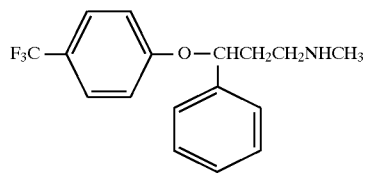

and pharmaceutically acceptable acid addition salts thereof.

BACKGROUND OF THE INVENTION

N-methyl-3-(p-trifluoromethylphenoxy)-3-phenyl-propylamine or fluoxetine is a known substance acting on the central nervous system.

In particular, fluoxetine mainly possesses an antidepressant activity, due to its selective inhibitory effect on the serotonin uptake at a cerebral level.

The synthesis of this compound has been disclosed for the first time in U.S. Pat. No. 4,314,081.

Fluoxetine is currently one of the active ingredients more extensively prescribed by specialized physicians for treating several psychiatric diseases.

In fact, this active ingredient has many fields of use which range from treating anxiety, to the treatment of bulimia, as well as some forms of schizophrenia and sleep diseases.

A high demand for this medicament is matched by the requirement of the pharmaceutical industry to have processes of synthesis available which are more and more sophisticated and allow to obtain this active ingredient in a very pure form as well as high production yields.

The presence in the pharmaceutical formulation of the active ingredient in a form which is not highly pure can cause a non-completely satisfactory response to the treatment which leads the specialist to consider the possibility of changing the therapy.

These requirements have led the pharmaceutical companies to patent alternative processes of synthesis of fluoxetine, such as disclosed in EP 0 391 070, in which the final step of the process consists in subjecting 1-phenyl-3-(N-methylamino)propane-1-ol to an etherification with 1-chloro-4-trifluoromethylbenzene in the presence of potassium-t-butoxide as a base. The reaction is carried out in an organic solvent, such as N-methylpyrrolidone.

The aims targeted by the inventor in this document have not been completely achieved since the yields on industrial scale of the described process do not always reach high levels and, furthermore, the process entails high manufacturing costs since the reagent of potassium t-butoxide is much more expensive (more than 30 times) than a common base such as potassium hydroxide.

The use of a base (potassium t-butoxide) more expensive than hydroxides of alkaline metals is due to the fact that there is a technical prejudice in the art which advises against the use of a strong alkaline hydroxide as a base in the conditions of reaction disclosed in the afore-mentioned publication.

In fact, in accordance with the common knowledge on the chemistry of esters and amides, these compounds, in a strongly basic ambient due to alkaline hydroxides, are subject to a degradative reaction of saponification.

In view of this knowledge, the man skilled in the art would be induced to avoid the use of an amide-type solvent such as N-methyl-pyrrolidone together with a strong base such as alkaline hydroxides.

In EP 0 391 070 this drawback is avoided by using a strong base which does not give rise to a saponification, such as potassium t-butoxide, having an inert behavior with respect to the amidic solvent used, N-methyl-pyrrolidone.

A further drawback in carrying out the process in accordance with EP 0 391 070 is that using potassium t-butoxide in a solvent medium involves the risk of fire and explosion, as disclosed in Handbook of Reactive Chemical Hazards, Bretherick, pag. 293 (1985).

It is also known from WO 94/00416 to prepare fluoxetine by reacting N-methyl-3-hydroxy-3-(phenyl)propylamine with 1-chloro-4-(trifluoromethyl)benzene in dimethylsolfoxide in the presence of alkaline hydroxides, for 4–20 hours at 50°–120° C.

However, the performance of this process on industrial scale is not free from drawbacks mainly related to the use of dimethylsolfoxide (DMSO).

In fact, DMSO has high risks of handling, toxicity, and disposal, since it is a compound which is very difficult to recover.

Therefore, its use requires particular precautions and measures for the recovery of production residues/byproducts. Moreover, since the reaction environment has strong basic pH values and requires the use of large amounts of solvent at a temperature of about 100° C., in these conditions the risks of explosion and of plant safety are increased.

Furthermore, the disclosed yields do not have percentage values greater than 87–88%, even with longer processing times.

An aim of the present invention is to avoid or substantially attenuate the above-identified problems.

One of the objects of the present invention is to provide a process for preparing fluoxetine with high production yields, starting from basic reagents which are readily commercially available at a low cost.

Another object of the present invention is to provide a process for preparing fluoxetine which involves the use of reagents and solvents which can be easily handled, have low toxicity, do not explode under reaction conditions, and which therefore do not need particular precaution of use.

Not the least object is to provide a process of crystallization of fluoxetine hydrochloride which allows to obtain the active ingredient in the form of very pure crystals, with high production yields.

SUMMARY OF THE INVENTION

In view of this aim, as well as these and other objects of the invention which will become apparent hereinafter, there is provided a process for preparing N-methyl-3-(p-trifluoromethylphenoxy)-3-phenyl-propylamine of formula (I):

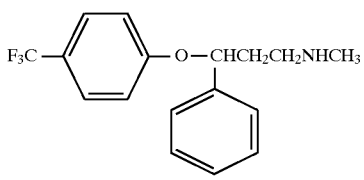

or pharmaceutically acceptable acid addition salts thereof, comprising reacting the compound 1-phenyl-3-(N-methylamino)propane-1-ol of the formula (II):

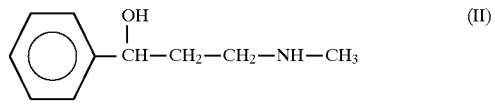

with 1-chloro-4-trifuoromethylbenzene of the formula (III):

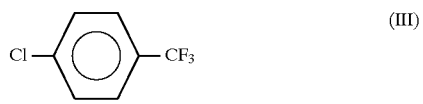

in the presence of a hydroxide of an alkaline metal in a non saponificable dipolar aprotic solvent.

DETAILED DESCRIPTION OF THE INVENTION

Amongst alkaline metal hydroxides the use of sodium hydroxide or potassium hydroxide is preferred, the latter being the preferred one.

Particularly preferred is potassium hydroxide containing from 8 to 12% by weight of water.

The reaction in accordance with the present invention is advantageously carried out at a temperature in the range of 80° to 110° C. for 2–15 hours, the highest yields being obtained in the preferred range of 90° to 100° C.

The aprotic dipolar solvents used in the present invention are organic compounds which contain as heteroatoms nitrogen or oxygen and are not subjected, under the reaction conditions in accordance with the present process, to a degradative reaction due to saponification.

The use of aprotic dipolar solvents containing sulfur is excluded from the scope of the present invention.

Said aprotic solvents are preferably amides or glymes.

Among available amidic solvents the most preferred ones are those completely substituted to the nitrogen atom, the most preferred ones being cyclic amides. In carrying out the process according to the present invention amides selected from the group consisting of N-methyl-pyrrolidone, 1-formil-piperidine, 1,1,3,3-tetramethylurea, 1,3 dimethyl-2-imidazolydinone are highly preferred, N-methyl-pirrolidone being the preferred one.

Glymes selected from the group consisting of ethylglyme ($CH_3CH_2$—O—$CH_2CH_2$—O—$CH_2CH_3$), diglyme $CH_3$—O—($CH_2CH_2$—O)$_2$—$CH_3$ and ethyldiglyma $CH_3CH_2$—O—($CH_2CH_2$—O)$_2$—$CH_2CH_3$ are particularly preferred in the present invention.

These solvents, besides having a favorable correlation between temperature and vapor pressure in the operating conditions of the present process, have low toxicity and can be eliminated by water extraction.

In carrying out the process according to the invention it is preferred to react 1-chloro-4-trifluoromethylbenzene in a slight excess with respect to 1-phenyl-3-(N-methylamino) propane-1-ol. In particular, high reaction yields are obtained by using 1.2–1.3 moles of 1-chloro-4-trifluoromethylbenzene per mole of aminic starting compound.

In accordance with a preferred embodiment of the process of the invention KOH 90% by weight is used in a molar ratio of 2.5:1 with respect of the starting aminic compound (II), by using N-methyl-pyrrolidone as solvent and working at temperatures of about 90° C.

The use in the present invention of aprotic dipolar solvents of the previously-disclosed type, at very high pH values of the reaction environment, is surprising, since, at these pH values, a degradative reaction by saponification of these solvents would be expected. In particular, it was observed that by using N-methyl-pyrrolidone as solvent phase, under the reaction conditions disclosed hereinbefore, additional saponification reactions do not take place, and the yields of the process are greater than 90%, namely greater than those obtained in accordance with the synthesis processes of the prior art.

The process in accordance with the present invention allows to obtain yields of about 94%, when all the reaction parameters are optimized.

A further advantage of the present invention with respect to some prior art processes consists in that sulfurated solvents are not used (such as DMSO).

The advantages are mainly linked to the fact that sulfurated solvents with a low oxidation number are stinking substances which require particular care during use in order to limit the environmental impact. Moreover, solvents with a high oxidation number have a high degree of chronic toxicity as a consequence of prolonged exposure, as occurs in the environments of the manufacturing plants.

The process in accordance with the present invention allows therefore to obtain fluoxetine by using reagents which are less toxic than those used in the process according to the prior art, thus minimizing the risk of causing problems from an ecological point of view.

The process according to the present invention advantageously includes a further step of conversion of the neo-synthetized fluoxetine in its hydrochloride, said step comprising reacting a HCl concentrated solution with a solution of fluoxetine in a toluenic phase in the presence of water until pH values of about 3 are obtained.

By way of example, a toluenic solution of crude fluoxetine obtained by the process disclosed hereinbefore, is subjected to an initial step of washing with water and then water is added to the resulting toluenic phase and subsequently a HCl concentrated solution (HCl 30–45%), until pH values of about 3 are achieved, a condition in which the precipitation of the fluoxetine hydrochloride is almost complete.

In accordance with another aspect the present invention a process for obtaining fluoxetine hydrochloride in the form of highly pure crystals is provided, said process comprising the crystallization of fluoxetine hydrochloride from a solvent system consisting of wet ethylacetate.

In particular, the crystallization process comprises an initial step in which fluoxetine hydrochloride is dissolved under heat in a water solution in ethylacetate, followed by distillation of some part of the solvent in order to remove water and a final step in which the fluoxetine solution in ethylacetate is cooled, until a white crystalline solid is formed.

The final step of crystallization allows to obtain fluoxetine hydrochloride in a highly pure form, by using a solvent which has low toxicity values.

The following examples are provided merely for illustrative purposes of the present invention and are not to be read as limiting the scope of protection of the present invention, as defined by the appended claims.

EXAMPLE 1

Synthesis of fluoxetine hydrochloride.

30 g of 1-phenyl-3-(N-methylamine)propane-1-ol and 150 ml of N-methyl-pyrrolidone are added in a 0.5 l flask under nitrogen atmosphere. When the solution has completely turned to yellow, 28.2 g of KOH 90.4% are added and a moderate exothermia is observed. Then, n-exane is added in an amount sufficient to have reflux at a temperature of 90° C. The inner temperature is raised at 90° C. under constant and azeothropic reflux, optionally by varying the amount of n-exane and in 1 hour 42.6 g of 1-chloro-4-trifluoromethylbenzene is added dropwise. It is observed that the flakes of potassium hydroxide dissolve completely, while a microcrystalline precipitate of KCl is obtained. The solution slowly turns to brown-orange. Stirring is continued for ten hours, while simultaneously monitoring the reaction by TLC. Initially, the reaction seems to be slightly exotermic. After 10 hours the control by TLC does not show traces of non reacted product. The temperature is then brought below 60° C. and 20,5 g of acetic acid 80% is carefully added. Vacuum is then slowly made and a mixture of solvents is distilled off until a temperature of 100° C. is reached at a residual pressure of 16 mm Hg. 22 ml of head (mainly n-exane) and 113 g of high boiling solvents (mainly N-methyl-pirrolidone) are thus recoverd. The temperature is then reduced to 0° C. and 240 ml of toluene is added to dilute. 100 ml of water is then slowly added dropwise in about 30 minutes under cooling. The aqueous phase containing salts, part of the reaction solvent and the non-reacted product of reaction is set aside; the organic phase is subjected to four washings with 100 ml of water. Then, 180 ml of water at ambient temperature are added to the toluenic phase and then about 16 ml of HCl 37% are slowly added dropwise at constant pH 3 (at this pH value fluoxetine is stable in these conditions). During acidification, the precipitation of the hydrochloride is observed. Temperature is then kept at 20° C. for 15 minutes till pH stabilization at the value of 3 (optionally by further adding HCl 37%). Temperature is then reduced to 0° C. and stirring is conducted at this temperature for at least two hours. A very pure crystalline product is obtained, which is quickly filtered, leaving in the mother liquor almost all the colour. The product is filtered off at 0° C. and then washed with 10 ml×3 of water at 0° C. and pH 7, then with 20 ml×4 of toluene.

The wet solid weight is 75,6 g which corresponds to 56,6 on a dry basis; m.p. 158°–159° C. (one spot TLC).

Yield=90.2% calculated on 1-phenyl-3-(N-methylamino) propane-1-ol (it is possible to recover a further 3.5–4% of product from the mother liquor).

EXAMPLE 2

Crystallization of fluoxetine hydrochloride.

30 g of crude fluoxetine hydrochloride obtained in accordance with Example 1 is heat dissolved in 300 ml of ethyl acetate and 4.5 g of water at reflux. Heat filtering is carried out by washing the filter with a hot mixture of 50 ml of ethyl acetate and 0.75 ml of water. The system is then made anhydrous by distilling off 170 ml of the solvent. 50 ml×3 of ethyl acetate are added (in three subsequent times) distilling off the same amount. Cooling is then allowed and crystallization takes place at 56° C. The stirrable slurry of white solid is brought to 20° C., kept at this temperature for 30 minutes, and then filtered and washed with 60 ml×2 of ethyl acetate.

One obtains: 28.88 g of wet product, 28.71 g of dry product (corresponding yield=95.7%).

The product collected from the filter is a white solid almost completely dry. The product has a single spot by TLC having m.p.=158°–159° C.

EXAMPLE 3

To a solution containing 30 kg of N-methyl-3-hydroxy-3-phenyl-propylamine in 150 l of 1,3-dimethyl-imidazolidinone containing in suspension 28 kg of 90% commercial potassium hydroxide, a small amount of n-exane (about 20 kg) is added, calibrated such that the reflux temperature of the mass is of 85° C. to 105° C. Then, 39 kg of 1-chloro-4-trifluoromethyl-benzene is added in about one hour, maintaining an azeothropic reflux and collecting the small amounts of condensing water, taking care of adjusting the amount of n-exane in the reaction mass, in case the temperature varies too much above or below of the set range. The reaction is completed in 5 to 10 hours (if necessary, it is possible to add a further 10% by weight of 1-chloro-4-trifluoromethyl-benzene reactant to convert a possibly too large amount of unreacted intermediate).

When the reaction is completed, the temperature lowers below 60° C. and 20.5 kg of acetic acid 80% is slowly added, to neutralize the free potassium hydroxide, then a vacuum of about 15 mm Hg is made and the reaction solvent is distilled under reduced pressure and collected.

Suitably, the maximum temperature of the boiler during the reaction does not exceed 115° C.

240 l of toluene is added to the residual mass followed by washing it with 100 l of water to completely eliminate the salts, the last traces of residual solvents and any unreacted intermediate due to its particular and surprising solubility in cold water. It is necessary to carry out these operations at room temperature since this intermediate is insoluble in hot water. The toluenic phase is then washed four times with 100 liters of water in order to complete this selective extraction: a highly purified toluenic phase is obtained which can be used as such for the final precipitation of the hydrochloride. To precipitate the hydrochloride it is sufficient to add 180 liters of water to the toluenic phase and then slowly add about 16 liters of a HCl aqueous solution at ambient temperature until a pH 3 in the aqueous phase is obtained. The product is then isolated at 0° C., by washing the solid first with ice-cold water to neutralization, and then with toluene. In the mother liquors less than 1% by weight of the product remains.

56–58 kg of the dry product is obtained which corresponds to a conversion of 89.2 to 92.4%.

EXAMPLE 4

To a solution containing 3 kg of N-methyl-3-hydroxy-3-phenyl-propylamine in 15 l of 1,1,3,3-tetramethyl-urea containing 2,8 kg of potassium hydroxide with a titre of 90% in suspension is added a small amount of n-exane (about 2 kg) calibrated such that the reflux temperature of the mass is between 85° and 100° C. Then, 3,9 kg of 1-chloro-4-trifluoromethyl-benzene is added in about 1 hour under azeothropic reflux and collecting aside the small amounts of water which condense, taking care of adjusting the exane amount in the reaction mass when the temperature varies too much below or above the set range. The reaction is completed in 5–10 hours (if necessary, it is possible to add a further 10% by weight of the 1-chloro-4-trifluoromethyl-benzene reagent to convert a too high amount of unreacted intermediate).

When the reaction is complete, the temperature is lowered below 60° C. and 2.1 kg of 80% acetic acid is carefully added to neutralize the free potassium hydroxide, then a vacuum of about 15 mm Hg is made and the reaction solvent is filtered off under reduced pressure to allow its recovery. Suitably, the maximum temperature of the boiler does not exceed 115° C. during this step.

24 l of toluene is added to the residual mass followed by washing it with 10 l of water to completely eliminate the salts, the last traces of residual solvent and the non reacted intermediate due to its particular and surprising solubility in cold water. It is necessary to carry out this step at room temperature since this intermediate is insoluble in hot water. The toluenic phase is then washed 4 times with 10 l of water to complete this selective extraction: a highly purified toluenic phase is obtained which can be used as such for the final precipitation of the hydrochloride. To precipitate the hydrochloride it is sufficient to add to the toluenic phase 18 l of water and then slowly add about 1.6 l of a hydrochloric acid aqueous solution at room temperature until the aqueous phase reaches pH value of 3. The product is then isolated at 0° C., by washing the solid first with ice-cold water to neutralization and then with toluene. In the mother liquors less than 1% of the product remains.

The yield of the dry product is of 5.5–5.7 kg which corresponds to a conversion of 87.6–90.8%.

EXAMPLE 5

To a solution containing 15 kg of N-methyl-3-hydroxy-3-phenyl-propylamine in 75 l of 1-formyl-piperidine containing in suspension 9 kg of sodium hydroxide with a titre >98%, a small amount of n-exane (about 10 kg) is added, calibrated such that the reflux temperature of the mass is between 90° and 100° C. Then, 18.6 kg of 1-chloro-4-trifluoromethyl-benzene is added in about 1 hour, maintaining an azeothropic reflux and collecting aside the small amounts of water which condenses, taking care of adjusting the exane amount in the reaction mass in case the temperature varies too much below or above the set range. The reaction is completed in 5–10 hours (if necessary, it is possible to add a further 10% by weight of the 1-chloro-4-trifluoromethyl-benzene reagent to convert a too high amount of unreacted intermediate).

When the reaction is complete, the temperature is lowered below 60° C. and 10.3 kg of 80% acetic acid is carefully added to neutralize the free potassium hydroxide, then a vacuum of about 15 mm Hg is made and the reaction solvent is filtered off under reduced pressure to allow its recovery. Suitably, the maximum temperature of the boiler does not exceed 115° C. during this step.

120 l of toluene is added to the residual mass followed by washing it with 50 l of water to completely eliminate the salts, the last traces of residual solvent and the non reacted intermediate due to its particular and surprising solubility in cold water. It is necessary to carry out this step at room temperature since this intermediate is insoluble in hot water. The toluenic phase is then washed 4 times with 50 l of water to complete this selective extraction: a highly purified toluenic phase is obtained which can be used as such for the final precipitation of the hydrochloride. To precipitate the hydrochloride it is sufficient to add to the toluenic phase 90 l of water and then slowly add about 8 l of a hydrochloric acid aqueous solution at room temperature until the aqueous phase reaches a pH value of 3. The product is then isolated at 0° C., by washing the solid first three times with 5 l of ice-cold water to neutralization, then 4 times with 10 l of toluene. In the mother liquors less than 1% by weight of the product remains.

28–29 kg of the dry product is obtained which correspond to a conversion of 89.2–92.4%.

What is claimed is:
1. A process for preparing N-methyl-3-(p-trifluoromethylphenoxy)-3-phenylpropylamine of formula (I):

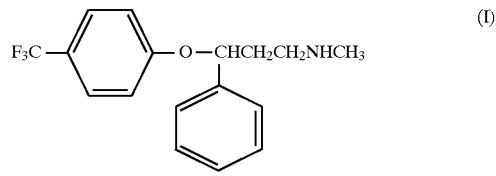

or addition salts thereof with a pharmaceutically acceptable acid, comprising reacting 1-phenyl-3-(N-methylamino) propane-1-ol of formula (II):

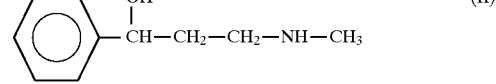

with 1-chloro-4-trifluoromethylbenzene of formula (III)

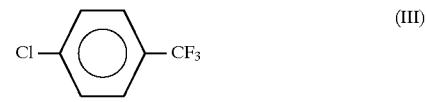

in the presence of an alkaline metal hydroxide in a non saponifiable dipolar aprotic solvent containing as heteroatoms nitrogen or oxygen, with the proviso that sulfur containing dipolar aprotic solvents are excluded.

2. A process according to claim 1, wherein said dipolar aprotic solvent is an amide or a glyme.

3. A process according to claim 1, wherein said solvent is a fully substituted amide.

4. A process according to claim 3, wherein said fully substituted amide is selected from the group consisting of N-methyl-pirrolidone, 1-formil-piperidine, 1,1,3,3 tetramethylurea, 1,3 dimethyl-2-imidazolidinone.

5. A process according to claim 2, wherein said glyme is selected from the group consisting of ethyl glyme, diglyme, and ethyl diglyme.

6. A process according to claim 1, wherein said metal alkaline hydroxide is selected from the group consisting of potassium hydroxide and sodium hydroxide.

7. A process according to claim 6, wherein said alkaline metal hydroxide is potassium hydroxide.

8. A process according to claim 1, wherein the temperature range is between 80° and 110° C.

9. A process according to claim 8, wherein said temperature is between 90° and 100° C.

10. A process according to claim 1, wherein the operative time is between 2 and 15 hours.

11. A process according to claim 1, further comprising a step of converting fluoxetine in its hydrochloride salt.

12. A process according to claim 11, wherein said conversion comprises reacting a concentrated HCl solution in a fluoxetine solution in a toluenic phase in the presence of water, until a pH value in proximity of 3 is obtained.

13. A process for preparing fluoxetine hydrochloride in a highly pure crystalline form, comprising heat dissolving fluoxetine hydrochloride in an aqueous solution of ethyl acetate, distilling part of the solvent to eliminate water and cooling the solution of fluoxetine in ethyl acetate, to form a white crystalline solid.

* * * * *